US009936692B2

(12) United States Patent
Sharma et al.

(10) Patent No.: US 9,936,692 B2
(45) Date of Patent: Apr. 10, 2018

(54) ENGINEERED PARTICULATE SYSTEMS FOR CONTROLLED RELEASE OF PESTICIDES AND REPELLANTS

(71) Applicant: UNIVERSITY OF FLORIDA RESEARCH FOUNDATION, INC., Gainesville, FL (US)

(72) Inventors: Parvesh Sharma, Gainesville, FL (US); Aarthi Narayanan, Naperville, IL (US); Hassan E. El-Shall, Gainesville, FL (US); Brij M. Moudgil, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 149 days.

(21) Appl. No.: 14/378,864

(22) PCT Filed: Feb. 14, 2013

(86) PCT No.: PCT/US2013/026123
§ 371 (c)(1),
(2) Date: Aug. 14, 2014

(87) PCT Pub. No.: WO2013/123176
PCT Pub. Date: Aug. 22, 2013

(65) Prior Publication Data
US 2015/0056259 A1 Feb. 26, 2015

Related U.S. Application Data

(60) Provisional application No. 61/598,698, filed on Feb. 14, 2012.

(51) Int. Cl.
*A01N 25/12* (2006.01)
*A01N 25/26* (2006.01)
*A01N 25/30* (2006.01)
*A01N 65/42* (2009.01)

(52) U.S. Cl.
CPC ............. *A01N 25/26* (2013.01); *A01N 25/12* (2013.01); *A01N 25/30* (2013.01); *A01N 65/42* (2013.01)

(58) Field of Classification Search
None
See application file for complete search history.

(56) References Cited

U.S. PATENT DOCUMENTS

| 6,027,740 | A  | * | 2/2000  | Puterka ............... A01G 7/00 424/405 |
| 6,261,997 | B1 |   | 7/2001  | Rubin et al. |
| 6,857,224 | B1 | * | 2/2005  | Kammereck ........... A01N 3/00 47/24.1 |
| 7,030,062 | B2 |   | 4/2006  | Nir et al. |
| 2006/0252649 | A1 | * | 11/2006 | Pluta .................. A01N 25/08 504/367 |
| 2007/0037711 | A1 | * | 2/2007  | Pluta .................. A01N 25/10 504/358 |
| 2007/0037732 | A1 | * | 2/2007  | Heltovics ............... A61Q 13/00 512/1 |
| 2009/0324506 | A1 |   | 12/2009 | Seidling et al. |
| 2010/0004132 | A1 |   | 1/2010  | Kepert et al. |
| 2010/0323897 | A1 |   | 12/2010 | Burke |
| 2011/0301369 | A1 |   | 12/2011 | Lin et al. |
| 2012/0183588 | A1 | * | 7/2012  | Supamahitorn ........ A01N 25/04 424/401 |

FOREIGN PATENT DOCUMENTS

WO    WO 2010-065996    6/2010

OTHER PUBLICATIONS

Lee et al., Journal of Colloid and Interface Science (2005), vol. 284, pp. 667-673.*
Daniel, C. et al. "Processed kaolin as an alternative insecticide against the European pear sucker, *Cacopsylla pyri* (L.)," *Journal of Applied Entomology*, 2005, pp. 363-367, vol. 129, No. 7.
Eigenbrode, S. D. et al. "Effects of Hydrophilic and Hydrophobic Kaolin-Based Particle Films on Pea Aphid (Homoptera: Aphididae) and Its Entomopathogen *Pandora neoaphidis* (Entomophthorales: Entomophthoraceae)" *Journal of Economic Entomology*, 2006, pp. 23-31, vol. 99, No. 1.
Hall, D. G. et al. "Effects of a Particle Film on Biology and Behavior of *Diaphorina citri* (Hemiptera Psyllidae) and Its Infestations in Citrus," *Journal of Economic Entomology*, 2007, pp. 847-854, vol. 100, No. 3.
Knight, A. L. et al. "Impacts of seasonal kaolin particle films on apple pest management," *The Canadian Entomologist*, 2001, pp. 413-428, vol. 133, No. 3.
Lapointe, S. L. et al. "Reduced Oviposition by *Diaprepes abbreviatus* (Coleoptera: Curculionidae) and Growth Enhancement of Citrus by Surround Particle Film," *Journal of Economic Entomology*, 2006, pp. 109-116, vol. 99, No. 1.
Liang, G. et al. "Repellency of a Kaolin Particle Film, Surround, and a Mineral Oil, Sunspray Oil, to Silverleaf Whitefly (Homoptera: Aleyrodidae) on Melon in the Laboratory," *Journal of Economic Entomology*, 2002, pp. 317-324, vol. 95, No. 2.
Mann, R. S. et al. "Sulfur volatiles from *Allium* spp. affect Asian citrus psyllid, *Diaphorina citri* Kuwayama (Hemiptera: Psyllidae), response to citrus volatiles," *Bulletin of Entomological Research*, 2011, pp. 89-97, vol. 101.

(Continued)

Primary Examiner — Hasan Ahmed
Assistant Examiner — Frank Choi
(74) Attorney, Agent, or Firm — Saliwanchik, Lloyd & Eisenschenk (57) ABSTRACT

Nanoengineered particulate coatings (NPCs) comprise a multiplicity of particulate hosts that are infused with a nanophase comprising a surfactant and at least one guest. The particulate hosts can be clay particles, the surfactant can be a cationic surfactant, and the guest can be an insect repellant. For example, montmorillonite particles infused with hexadecyl trimethyl ammonium bromide and garlic oil form NPCs that may be used to form an emulsion or suspension for spraying on citrus trees to repel Asian Citrus Psyllid.

9 Claims, 8 Drawing Sheets

(56) References Cited

OTHER PUBLICATIONS

Podskalska, H. et al. "Use of infochemicals to attract carrion beetles into pitfall traps," *Entomologia Experimentalis et Applicata*, 2009, pp. 59-64, vol. 132, No. 1.

Puterka, G. J. et al. "Progress Toward Liquid Formulations of Particle Films for Insect and Disease Control in Pear," *Environmental Entomology*, 2000, pp. 329-339, vol. 29, No. 2.

Puterka, G. J. et al. "Action of Particle Films on the Biology and Behavior of Pear Psylla (Homoptera: Psyllidae)," *Journal of Economic Entomology*, 2005, pp. 2079-2088, vol. 98, No. 6.

Showler, A. T. "Effects of Kaolin-Based Particle Film Application on Boll Weevil (Coleoptera: Curculionidae) Injury to Cotton," *Journal of Economic Entomology*, 2002, pp. 754-762, vol. 95, No. 4.

Unruh, T. R. et al. "Particle Films for Suppression of the Codling Moth (*Lepidoptera tortricidae*) in Apple and Pear Orchards," *Journal of Economic Entomology*, 2000, pp. 737-743, vol. 93, No. 3.

Jatav, S. et al., "Chemical Stability of Laponite in Aqueous Media", *Appl. Clay Sci.*, (2014) pp. 72-77, vol. 97-98.

Safety Data Sheet for TIXOGEL-MP 100, Revision Date Dec. 15, 2016, pp. 1-12.

Bhattacharyya, K.G. et al., "Adsorption of a few heavy metals on natural and modified kaolinite and montmorillonite: A review," *Advances in Colloid and Interface Science*, Sep. 2008, pp. 114-131, vol. 140.

\* cited by examiner

ENGINEERED PARTICULATE SYSTEMS FOR CONTROLLED RELEASE OF PESTICIDES AND REPELLANTS

CROSS-REFERENCE TO RELATED APPLICATIONS

This application is the U.S. national stage application of International Patent Application No. PCT/US2013/026123, filed Feb. 14, 2013, which claims the benefit of U.S. Provisional Application Ser. No. 61/598,698, filed Feb. 14, 2012, the disclosures of which are hereby incorporated by reference herein in their entireties, including any figures, tables, or drawings.

BACKGROUND OF INVENTION

Insect attack of many fruits such as apples, citrus, and pears seriously affects the food industry. For instance, citrus greening is one of the most serious diseases threatening the $9.3 B Florida citrus industry. With no known cure, millions of trees have been removed from the citrus groves in order to prevent the spread of the disease. The loss of the citrus crop is estimated at 25% of a total $2.5 billion value for all U.S. citrus. The insect Asian Citrus Psyllid (ACP), carrier of bacterial species *candidatus liberibacter asiaticus*, spreads citrus greening, also known as the Huanglongbing (HLB) disease, primarily by feeding on citrus crops. In this process, the insect relies mainly on settling and olfactory cues. Current disease management methods have failed to stop, and are only partially successful in slowing, the ACP/HLB infestation due to a lack of known resistant cultivars, biological control agents, and cultural control options. Broad spectrum insecticides are currently the primary insect control options.

Particle film technology has emerged as a pesticide-less, environmentally friendly, and potentially economically sustainable approach to protect plants from insects. Although this technology has been used with some success for suppression of insect pests in apple and pear crops, it suffers from limitations, particularly: (i) insect attack in developing gaps created as a consequence of growth of existing leaves; (ii) insect attack on new unprotected flush and (iii) non-selective and poor adhesion of particles to leaves.

Particle films comprising hydrophilic and hydrophobic kaolin clays have been used for control of insects, such as, pear psylla, *Cacopsylla pyricola* Foerster, on pear (*Prunus* spp.)[1] codling moth, *Cydia pomonella* (L.), on apple (*Malus* spp.)[2]; boll weevil, *Anthonomus grandis grandis*, Boheman, on cotton, *Gossypium hirsutum* L.,[3] and European pear sucker, *Cacopsylla pyri* (L.). on pear (*Prunus* spp.)[4]. This technology is proving to be economically viable for suppression of pests in apples and pears[2,5]. Studies on the use of particle films for the suppression and biological effects of *D. citri* on citrus[6-8] have also been reported to have varying degree of success.

The main effect of a particle film barrier on plant foliage is to interfere with the visual cues as well as ability of insects to settle, feed, move, and oviposit[3, 9-11]. In some cases, the film suspensions were found to be toxic to insects[11], making toxicity an additional factor to be considered. Surface modified kaolin clay particle films have also been found to be effective against agricultural insects[10,12]. Surround WP (Engelhard Corp., Iselin, N.J.), a kaolin based formulation has shown to suppress infestations of nymph and adult *D. citri* in citrus trees by 31% and 61%, respectively, as compared with untreated trees[8]. Hall et al.[6] have reported a similar cumulative reduction in infestation by *D. citri* of 78% on mature leaves, and 60% on flush shoots when compared to untreated trees. Similarly, significant reduction in the number of eggs and nymphs per flush (~85%) in particle treated films is demonstrative of the effectiveness of the particle film approach in controlling the spread of HLB disease.

In spite of the success of the particle film technology, it suffers from major limitations. Puterka et al.[11] reports that the mortality of adult pear psylla on particle treated foliage is low, since the adults are able to feed through the films, indicating the need for a continuous coating. In addition, the growth of the leaves after the application of particle film can also cause gaps to develop, making the leaves vulnerable to ACP attack. Another significant issue, especially with respect to the citrus crops, is the exclusive preference of adult females (*D. citri*) for fresh flush and unexpanded leaves for oviposits. This is a challenging issue requiring frequent film application. This necessitates an alternative protective methodology for protection between particle film applications. An additional limitation of the current particle film technology is the lack of rain fastness. Hall et al.[6] have reported that more than 15 cm of cumulative rain completely negated the suppressive effect of Surround treatment. Combined with the visual observation that the particle film does not appear to adhere to the fresh flush as much it does to the mature leaves, this suggests that technological challenges must be overcome for extending the efficacy of particle film barrier to psyllid attack.

Insect repellents, such as plant derived essential oils, are an attractive means for pest management as they are considered minimum risk pesticides and exempt from EPA registration. In a recent report[13], efficiency of crushed garlic chive leaves and garlic chive essential oil in repelling *D. citri* adults and a comparison to wild onion plants and crushed wild onion leaves has indicated promise. Similar mixture of components are found to be effective against other insect species[14]. In spite of the utility of essential oils to protect crops, they find limited application in fields due to the oils high volatility and lack of stability, which limits their effectiveness to shorter durations and necessitating frequent applications.

Hence there remains a need for an effective particle film technology that: (i) provides a continuous protection to the foliage during the growth and leaves expansion stages, thereby preventing psyllid attacks in developing gaps in particle films; and (ii) adheres to fresh flush and mature leaves and withstands weathering.

1. Puterka G J, Glenn D M M, Sekutowski D G, Unruh T R, Jones S K. Progress toward liquid formulations of particle films for insect and disease control in pear. *Environmental Entomology* 2000; 29(2):329-39
2. Unruh T R, Knight A L, Upton J, Glenn D M, Puterka G J. Particle films for suppression of the codling moth (Lepidoptera: Tortricidae) in apple and pear orchards. *Journal Of Economic Entomology* 2000; 93(3):737-43
3. Showier A T. Effects of kaolin-based particle film application on boll weevil (Coleoptera: Curculionidae) injury to cotton. *Journal Of Economic Entomology* 2002; 95(4): 754-62
4. Daniel C, Pfammatter W, Kehrli P, Wyss E. Processed kaolin as an alternative insecticide against the European pear sucker, *Cacopsylla pyri* (L.). *Journal of Applied Entomology* 2005; 129(7):363-7
5. Knight A L, Christianson B A, Unruh T R Impacts of seasonal kaolin particle films on apple pest management. *Canadian Entomologist* 2001; 133(3):413-28

6. Hall D G, Lapointe S L, Wenninger E J. Effects of a particle film on biology and behavior of *Diaphorina citri* (Hemiptera: Psyllidae) and its infestations in citrus. *Journal of Economic Entomology* 2007; 100(3):847-54
7. Lapointe S L, McKenzie C L, Hall D G. Reduced oviposition by Diaprepes abbreviatus (Coleoptera: Curculionidae) and growth enhancement of citrus by surround particle film. *Journal of Economic Entomology* 2006; 99(1):109-16
8. McKenzie C L, Lapointe S L, Hunter W B, Puterka G J. Efficacy of Surround for control of Asian citrus psyllid on citrus. *Arthropod Management Tests* 27 2000; D8
9. Glenn D M, Puterka G J. Particle films: a new technology for agriculture. *Horticultural Reviews* 2005; 31:1-44
10. Liang G, Liu T X. Repellency of a kaolin particle film, surround, and a mineral oil, Sunspray oil, to silverleaf Whitefly (Homoptera: Aleyrodidae) on melon in the laboratory. *Journal of Economic Entomology* 2002; 95(2): 317-24
11. Puterka G J, Glenn D M, Pluta R C. Action of particle films on the biology and behavior of pear psylla (Homoptera: Psyllidae). *Journal of Economic Entomology* 2005; 98(6):2079-88
12. Eigenbrode S D, Ding H J, Neufeld J, Duetting P. Effects of hydrophilic and hydrophobic kaolin-based particle films on pea aphid (Homoptera: Aphididae) and its entomopathogen Pandora neoaphidis (Entomophthorales: Entomophthoraceae). *Journal of Economic Entomology* 2006; 99(1):23-31
13. Mann R S, Rouseff R L, Smoot J M, Castle W S, Stelinski L L. Sulfur volatiles from *Allium* spp. affect Asian citrus psyllid, *Diaphorina citri* Kuwayama Hemiptera: Psyllidae), response to citrus volatiles. *Bulletin of Entomological Research* 2010; doi: 10.1017/S0007485310000222:1-9
14. Podskalska H, Ruzicka J, Hoskovec M, Salek M. Use of infochemicals to attract carrion beetles into pitfall traps. *Entomologia Experimentalis Et Applicata* 2009; 132(1): 59-64

DETAILED DISCLOSURE

Embodiments of the invention are directed to nanoengineered particulate coatings (NPCs) comprising clay particles that act as a host for impregnation with a guest that can be released as a volatile in the presence of air, or leached into a liquid when the NPCs are dispersed in the liquid. In an embodiment of the invention, the NPC's guest is an insect repellent. The NPCs can be dispersed on a plant to allow the guest to be slowly released over an extended effective duration to prevent attack on emerging gaps during the growth of the plant. In these exemplary embodiments of the invention directed to release of agricultural agent over a period during which a plant grows, NPCs are hydrophobic in character, which allows adequate coating of leaves that withstand weather fluctuations. In addition to insect repellants, the NPCs can be combined with other treatment options, such as systemic application of insecticides, to effectively manage agricultural diseases. NPCs allow slow release of insecticides, pesticides, fertilizers or their combination.

As the applicability of clays depend on their physicochemical properties, properties that must be considered include the mineral fabric, surface area, porosity, crystal morphology, structure and composition of the clays. In embodiments of the invention, hydrophilic clays, such as montmorillonite, can be modified to make them hydrophobic by the use of cationic surfactants, such as hexadecyl trimethyl ammonium bromide, or Food and Drug Administration (FDA) approved cetyl pyridinium chloride. According to an embodiment of the invention, repellents are encapsulated in the montmorillonite clays from an aqueous system that uses cationic surfactants. In one method, according to an embodiment of the invention, montmorillonite clay particles are modified with cationic surfactants to make them hydrophobic, and the hydrophobic clay is used to encapsulate repellents and, optionally, hydrophobic dyes. The modification of clays is carried out under aqueous conditions without the use of organic solvents. Hydrophobic dyes and repellents that can be encapsulated, according to embodiments of the invention, include Sudan III, garlic oil and anionic dyes, such as acid blue 74.

Another embodiment of the invention is a method where hydrophobic modification and encapsulation of the dye and/or repellent occurs upon simultaneous addition of surfactant and the dye and/or repellent to hydrophilic clay. For example, garlic oil and Sudan III are encapsulated in unmodified montmorillonite in the presence of hexadecyl trimethyl ammonium bromide to form NPCs, according to an embodiment of the invention.

NPCs with up to 40% (w/w) or more garlic oil in montmorillonite clays can be prepared. This quantity is more than twice the approximately 20% (w/w) garlic oil that can be absorbed in unmodified clays. According to embodiments of the invention, the NPCs display a release profile for garlic oil that is extended and slow compared to pure garlic oil. Release of the encapsulated insect repellent occurs over 2-3 months, which is dramatically longer than the 2 days for pure garlic oil.

According to embodiments of the invention, NPCs comprise an encapsulated non-polar guest, such as, garlic oil and hydrophobic dye Sudan III, and anionic pesticides, repellents, and/or dyes, such as acid blue 74. NPCs can contain a plurality of hydrophobic herbicides, such as, alachlor, and anionic herbicides, such as, sulfometuron.

In embodiments of the invention, a co-guest can be included in the host NCPs to further modify the rate of release of the guest from the NCPs. In one embodiment, a co-guest that is more volatile than the guest is included to entrain the guest from the NCPs at a greater rate than when the guest is exclusively the repellant. In this embodiment, a poorly volatile guest can have its release rate improved to an acceptable level for its application. In another embodiment of the invention, a co-guest that is less volatile than the guest is included to diminish the volatility of the guest, and in this manner extend the length of release, particularly when low levels of the host are effective for the intended use, for example, as a repellant.

Figure 1A:
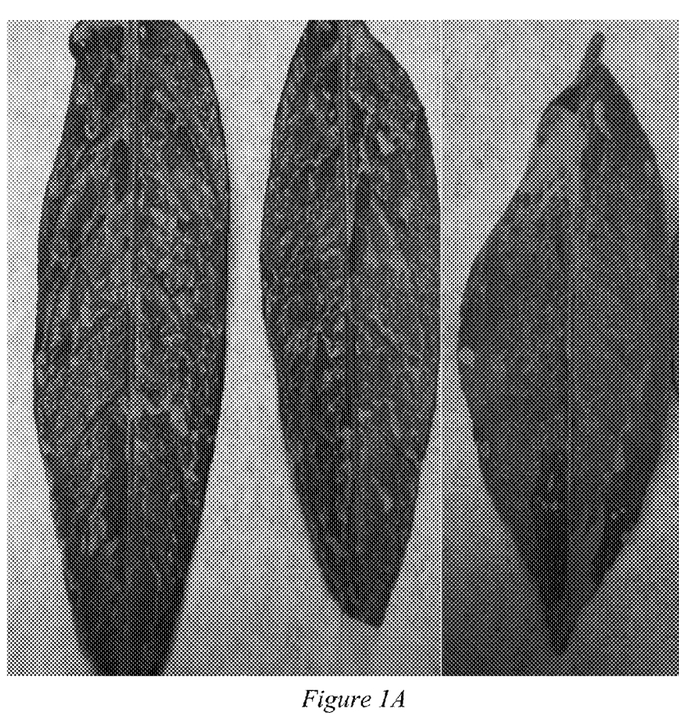
FIG. 1 shows photographs of a) citrus leaves covered with NCPs by spraying from a aqueous 5% methanol solution, according to an embodiment of the invention, b) the leaves after a single washing with water, and c) the leaves after three washings with water.
Figure 1B:
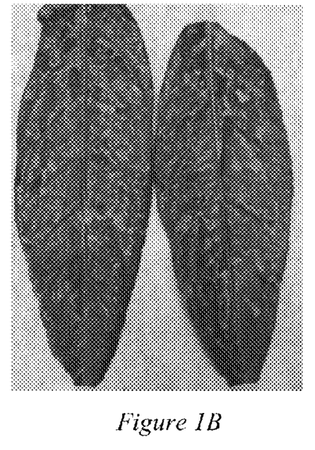
Figure 1C:
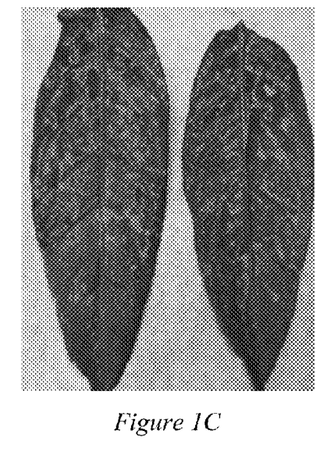
Figure 2:
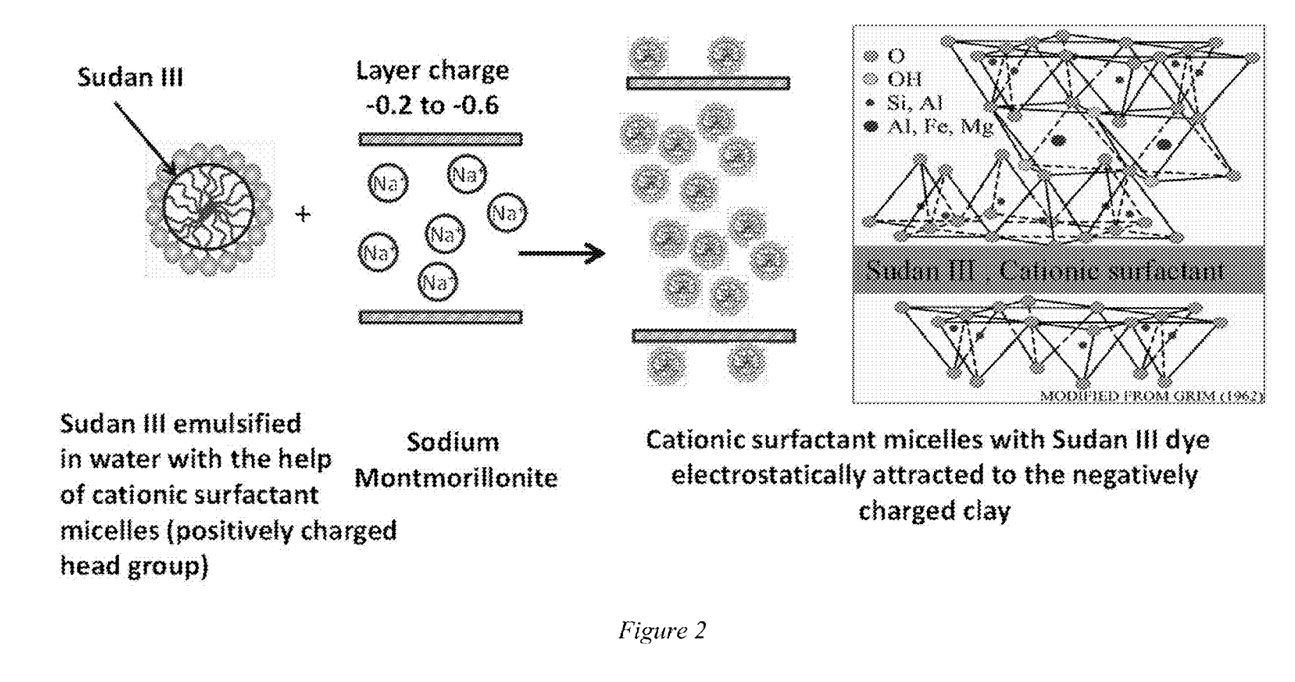
FIG. 2 shows a schematic for encapsulation of a hydrophobic dye (Sudan III) in montmorillonite clay, according to an embodiment of the invention.
Figure 3:
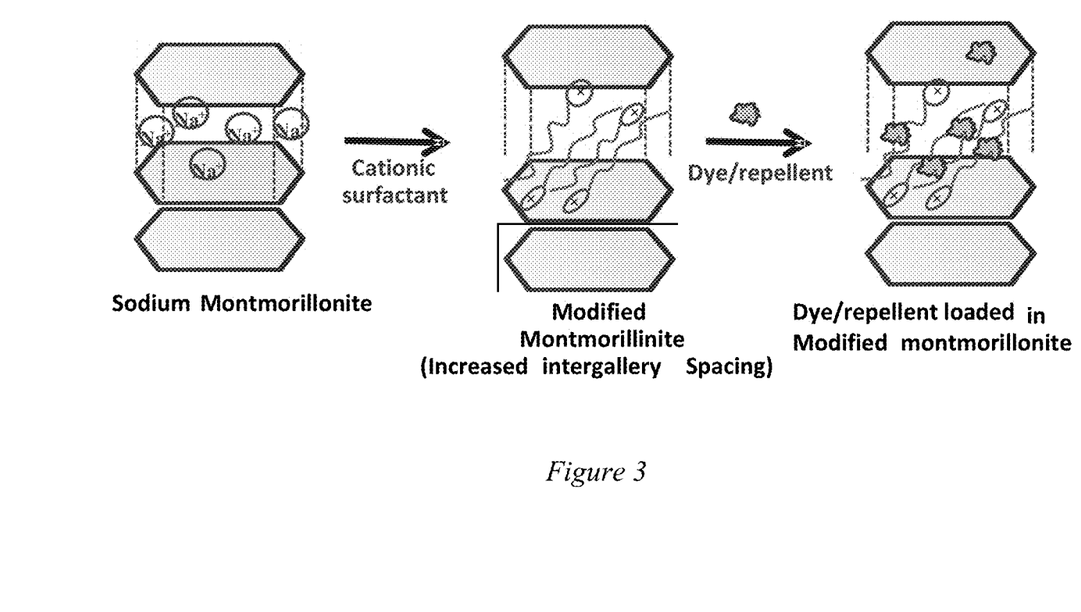
FIG. 3 shows a schematic for encapsulation of dye and/or repellent in montmorillonite clay, according to an embodiment of the invention.
Figure 4A:
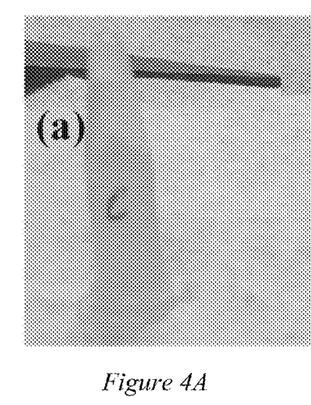
FIG. 4 shows photographic reproductions of Sudan III solubilized in clove oil on (a) unmodified montmorillonite and (b) montmorillonite in the presence of a cationic surfactant, according to an embodiment of the invention.
Figure 4B:
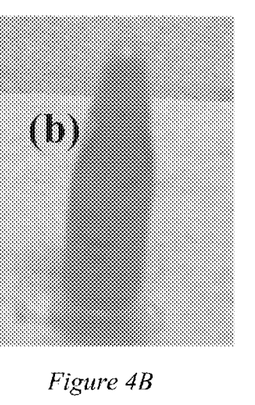
Figure 5A:
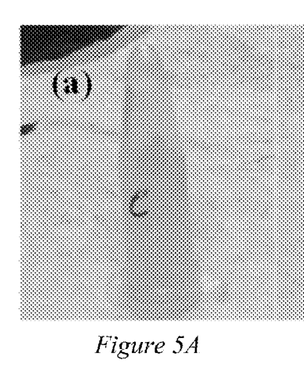
FIG. 5 shows photographic reproductions of Sudan III solubilized in clove oil on (a) unmodified montmorillonite and (b) modified montmorillonite (Claytone® 40), according to an embodiment of the invention.
Figure 5B:
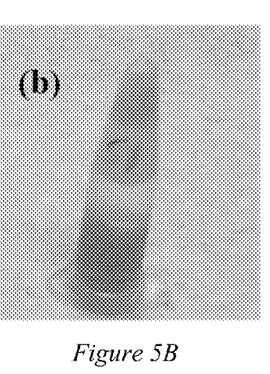
Figure 6:
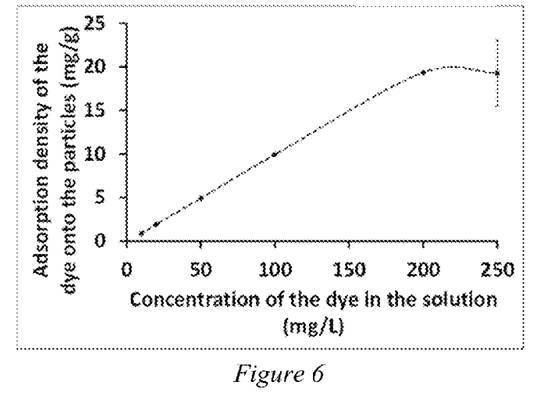
FIG. 6 is a plot of the adsorption isotherm for Acid blue 74 (anionic dye) on modified montmorillonite (Claytone® 40), according to an embodiment of the invention, where the standard deviations of two independent samples is shown at the last point.
Figure 7:
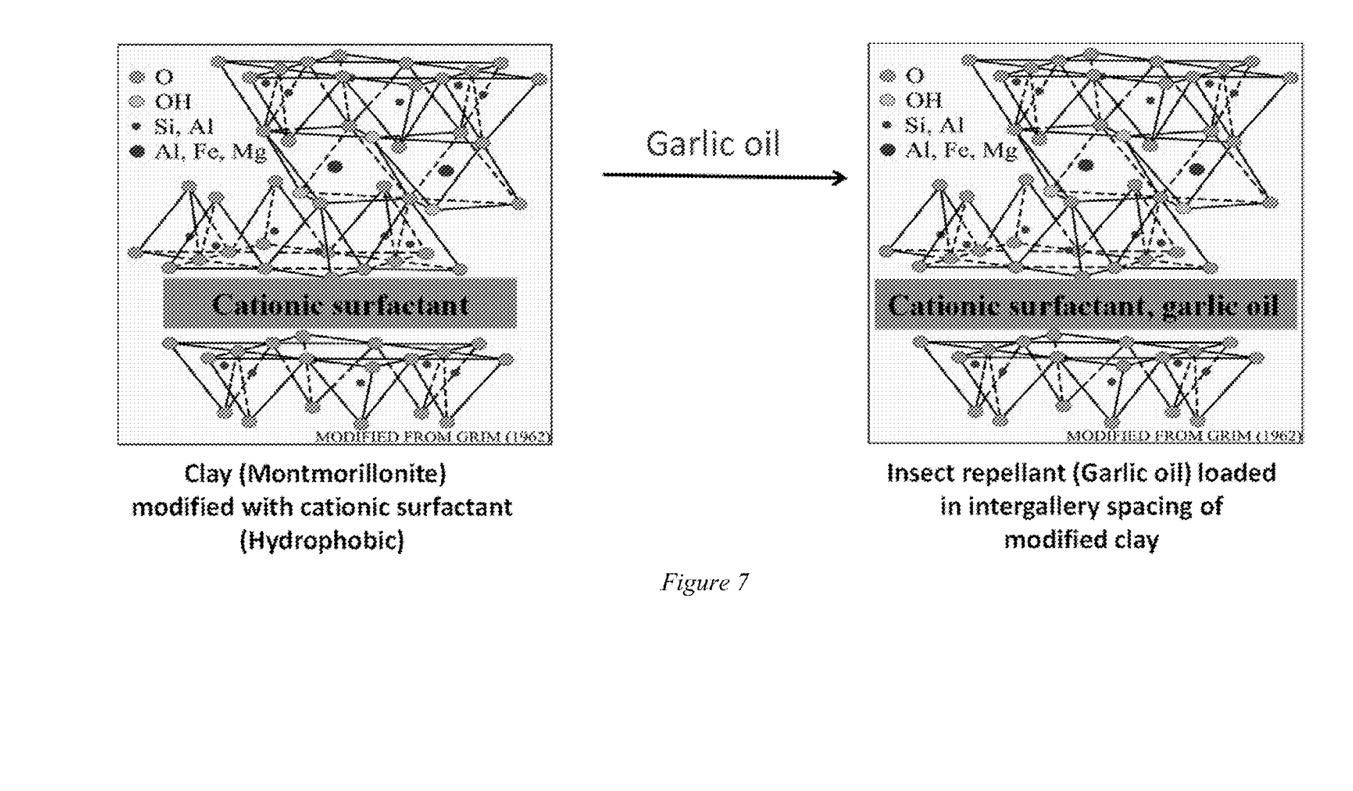
FIG. 7 shows a schematic for the encapsulation of garlic oil in organically modified montmorillonite, according to an embodiment of the invention.
Figure 8:
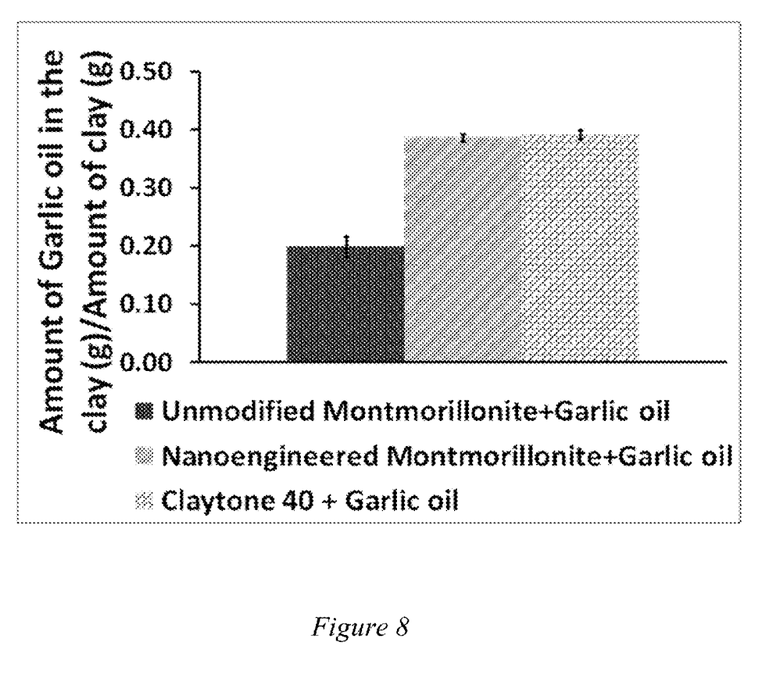
FIG. 8 shows a bar graph for the uptake of garlic oil in: unmodified montmorillonite; unmodified montmorillonite with a cationic surfactant (labeled as nanoengineered montmorillonite); and Claytone® 40, according to an embodiment of the invention, where the initial mass of garlic oil was 0.43 g and the initial mass of clay was 1 g with the standard deviation for three independent samples indicated on the bars.
Figure 9:
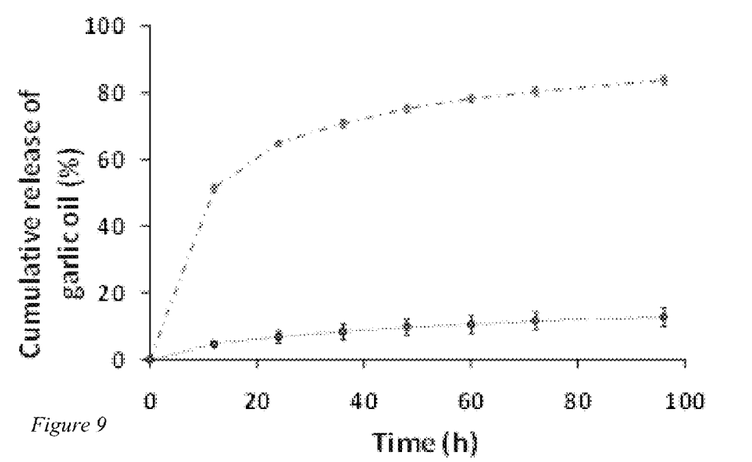
FIG. 9 shows plots of the cumulative release of neat garlic oil, +, and garlic oil from Claytone® 40, ●, according to an embodiment of the invention, where the initial amount of garlic oil in Claytone® 40 was 0.19 g and the release was 13% after 96 hours, while the release from neat garlic oil was 84% after 96 hours, with the initial amount of garlic oil being 0.2 g, and where the standard deviation for three independent samples is indicated.
Figure 10:
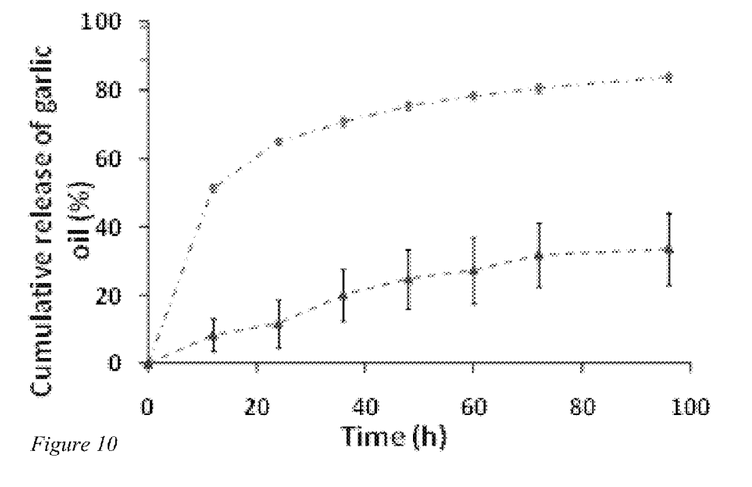
FIG. 10 shows plots of the cumulative release from neat garlic oil, +, and garlic oil from unmodified montmorillonite (free of surfactant), ▲, where the initial amount of garlic oil was 0.05 g and release was 34% after 96 hours, and release from neat garlic oil was 84% after 96 hours, with the initial amount of garlic oil being 0.2 g, and where the standard deviation for three independent samples is indicated.
Figure 11:
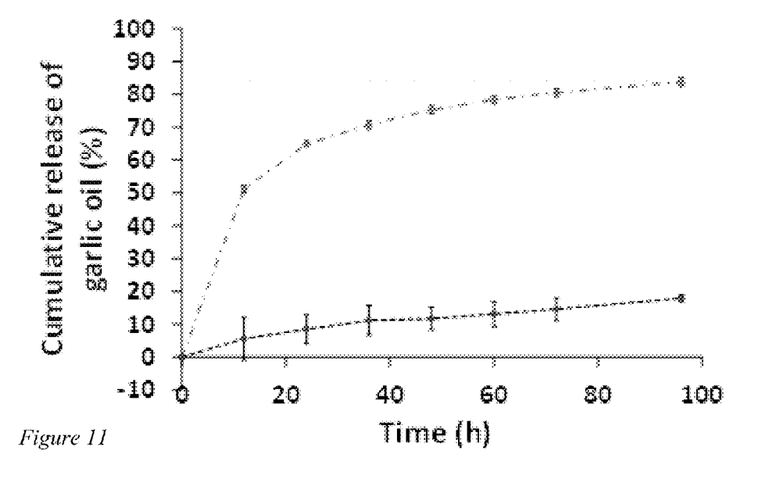
FIG. 11 shows plots of the cumulative release from neat garlic oil, ▲, and garlic oil from nanoengineered montmorillonite with a cationic surfactant, ♦, according to an embodiment of the invention, where the initial amount of garlic oil in nanoengineered montmorillonite was 0.19 g and its release of garlic oil was 18% after 96 hours, and the release from neat garlic oil was 84% after 96 hours, with the initial amount of garlic oil being 0.2 g, and where the standard deviation for three independent samples is indicated.
Figure 12:
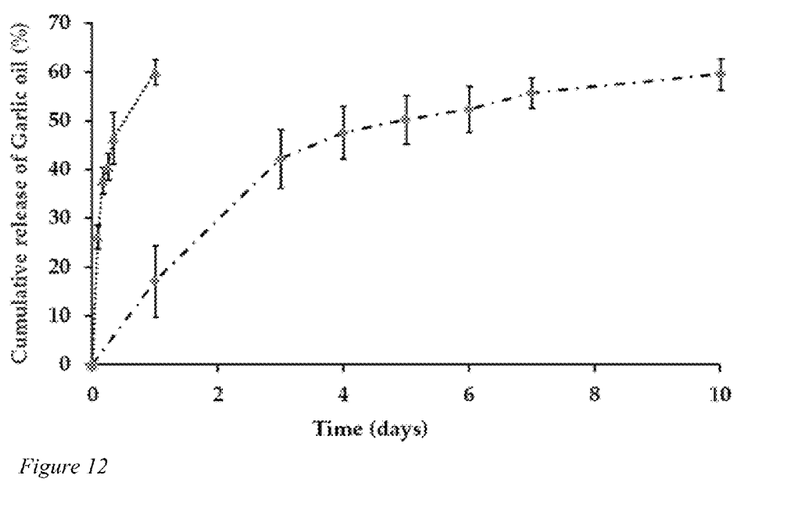
FIG. 12 shows plots of: the release under real world conditions in the field for neat garlic oil, ▲, where the initial amount of garlic oil was 0.6 g with release of 0.36 g in 1 day; and garlic oil from nanoengineered montmorillonite, ♦, according to an embodiment of the invention, where the initial amount of garlic oil was 0.6 g in 0.6 g of nanoengineered montmorillonite, which released 0.36 g of garlic oil in 10 days.

In embodiments of the invention, the NCPs are dispersed over a wide area as an agricultural agent. The NCPs can be distributed as an emulsion by spraying. The emulsion can comprise the NCPs and water or an aqueous solution, or can be an emulsion comprising water and a non-soluble organic. The solution can comprise a volatile organic solvent that dissolves in water, for example, an alcohol, such as methanol or ethanol. The emulsion can be one where an organic solvent with an affinity for the NCPs enhances their dispersion in the liquid vehicle such that agglomerate size remains smaller than that which would clog a nozzle. FIG. 1*a*) shows a photograph of citrus leaves upon which NCPs were sprayed using a 5% methanol in water solution. Additionally, FIG. 1 shows photographs of the leaves after b) one and c) three water washings, which demonstrates the robustness of the NCPs adherence to the leaves.

Although the NCPs are directed toward the release of guests that are beneficial for repelling insects from growing plants, the invention is not so limited. In other embodiments of the invention, the NPCs act as a delivery system for other volatile guests, such as fragrances or pheromones, to be incorporated in cosmetic or other personal care formulations. In other embodiments of the invention where the guest is leachable into a liquid, NCPs can be employed for the controlled release of guests, for example, herbicides or nutrients, when deposited over a field.

In another embodiment of the invention, the NCPs are not infused with a guest, but act as a host for absorbing a guest from an environment. For example, in one embodiment, the NCPs can be used to absorb contaminants or toxins from waste water. In another embodiment, the NCPs can be used to absorb oil from an oil spill.

Methods and Materials

Garlic Oil Encapsulation

Garlic oil, 400 μL, was added to 10 mL of deionized water and sonicated for 1 minute to disperse and emulsify the oil phase in water. Modified montmorillonite clay, Claytone® 40, was added to the oil in water emulsion. The resulting suspension was stirred for 2 hours at room temperature. The oil loaded clay particles were separated by centrifugation and unabsorbed oil was removed in the supernatant. The particles were washed twice with deionized water to remove any oil trapped between the particles. All the supernatant solutions were combined and the amount of garlic oil was estimated.

Garlic oil, 400 μL, was added to 10 mL of deionized water and sonicated for 1 minute to disperse and emulsify the oil phase in water. The quaternary ammonium surfactant, hexadecyl trimethyl ammonium bromide, was added to the oil in water emulsion at a rate of 20 times its critical micellar concentration (CMC), followed by the addition of unmodified montmorillonite, where all data in figures and Table 1, below, for samples prepared by this method are labeled Nanoengineered Montmorillonite. The resulting suspension was stirred for 2 hours at room temperature. The oil loaded clay particles were separated by centrifugation and the unabsorbed oil was removed in the supernatant. The particles were washed twice with deionized water to remove any oil trapped between the particles. All the supernatant solutions were combined and the amount of garlic oil was estimated using Baeyer's test.

FIGS. 2 and 3 are illustrative of a proposed mechanism for the incorporation of a guest in a clay host by use of a surfactant. FIGS. 4 and 5 are of photographs that display the physical appearance of clays modified by the two methods of preparation. FIG. 6 is a plot of the distribution of a dye into clay. FIG. 7 indicates that the host is included in a surfactant phase of the surfactant treated clays, according to an embodiment of the invention. FIG. 8 indicates the relative uptake of untreated and surfactant treated clays. FIGS. 9-11 show release profiles for garlic oil incorporated in clays with and without surfactants over a 96 hour period. Table 1, below, gives the initial and final conditions and calculated rates of release of garlic oil from clays. The quantity of garlic oil was increased to 100% of the mass of the nanoengineered montmorillonite and release of garlic oil was followed over a two month period of time that experienced normal rainfall under real world conditions. Under these conditions, as shown in FIG. 12, the release from the 100% garlic oil loaded clay was at least ten times slower than neat garlic oil, which displayed a loss of more than 50% of the neat garlic oil in a single day. The loss of the equivalent quantity of garlic oil from that absorbed in an equal mass of clay required ten days.

TABLE 1

Initial and final mass of garlic oil in montmorillonite clay samples and calculated half life of garlic oil in the samples

| Sample | Initial mass of garlic oil (mg) | Mass of garlic oil after 96 h (mg) | Half-life of garlic oil in the sample (days) |
|---|---|---|---|
| Nanoengineered Montmorillonite | 196 ± 2 | 161 ± 2 | 32 ± 2 |
| Claytone ® 40 | 197 ± 4 | 172 ± 6 | 70 ± 38 |
| Unmodified Montmorillonite | 54 ± 4 | 34 ± 6 | 9 ± 6 |
| Garlic oil only | 200 ± 2 | 33 ± 3 | 0.8 ± 0.06 |

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. Nanoengineered particulate coatings (NPCs), comprising a multiplicity of montmorillonite particles and a nanophase of a cationic surfactant, and at least one guest absorbed in said particles releasable as a volatile in the presence of air, wherein the nanophase is infused within the montmorillonite particles to form hydrophobic NPCs, wherein the hydrophobic NPCs comprise as one of the at least one guest 20 to 40% (w/w) garlic oil, wherein the cation surfactant is hexadecyl trimethyl ammonium bromide, whereby a coating of the hydrophobic NPCs is rain resistant, and wherein the guest is released at a rate over a period of at least ten times that of the guest absent the nanophase.

2. The NCPs of claim 1, further comprising as one of the at least one guest a liquid that is more volatile than the garlic oil.

3. The NCPs of claim 1, further comprising as one of the at least one guest a liquid that is less volatile than the garlic oil.

4. A method of preparing NCPs according to claim 1, comprising combining the multiplicity of montmorillonite particles with the cationic surfactant and with the at least one guest, and wherein one of the at least one guest is said amount of garlic oil.

5. The method of claim 4, wherein combining the particulate multiplicity of montmorillonite particles with the cationic surfactant is carried out prior to combining the multiplicity of montmorillonite particles with the guest.

6. The method of claim 4, wherein combining the multiplicity of montmorillonite particles with the cationic surfactant is carried out simultaneously with combining the multiplicity of montmorillonite particles with the guest.

7. A method of dispersing NCPs according to claim 1, comprising spraying an emulsion or a suspension comprising a fluid and the NCPs according to claim 1.

8. The method of claim 7, wherein the fluid is a solution of methanol in water.

9. A method of repelling Asian Citrus Psyllid (ACP) from citrus trees, comprising:
   providing a multiplicity of NCPs according to claim 1;
   preparing an emulsion or suspension of the NCPs in a aqueous 5% methanol solution; and
   spraying the emulsion or suspension onto the surfaces of citrus trees.

* * * * *